Figure 1:
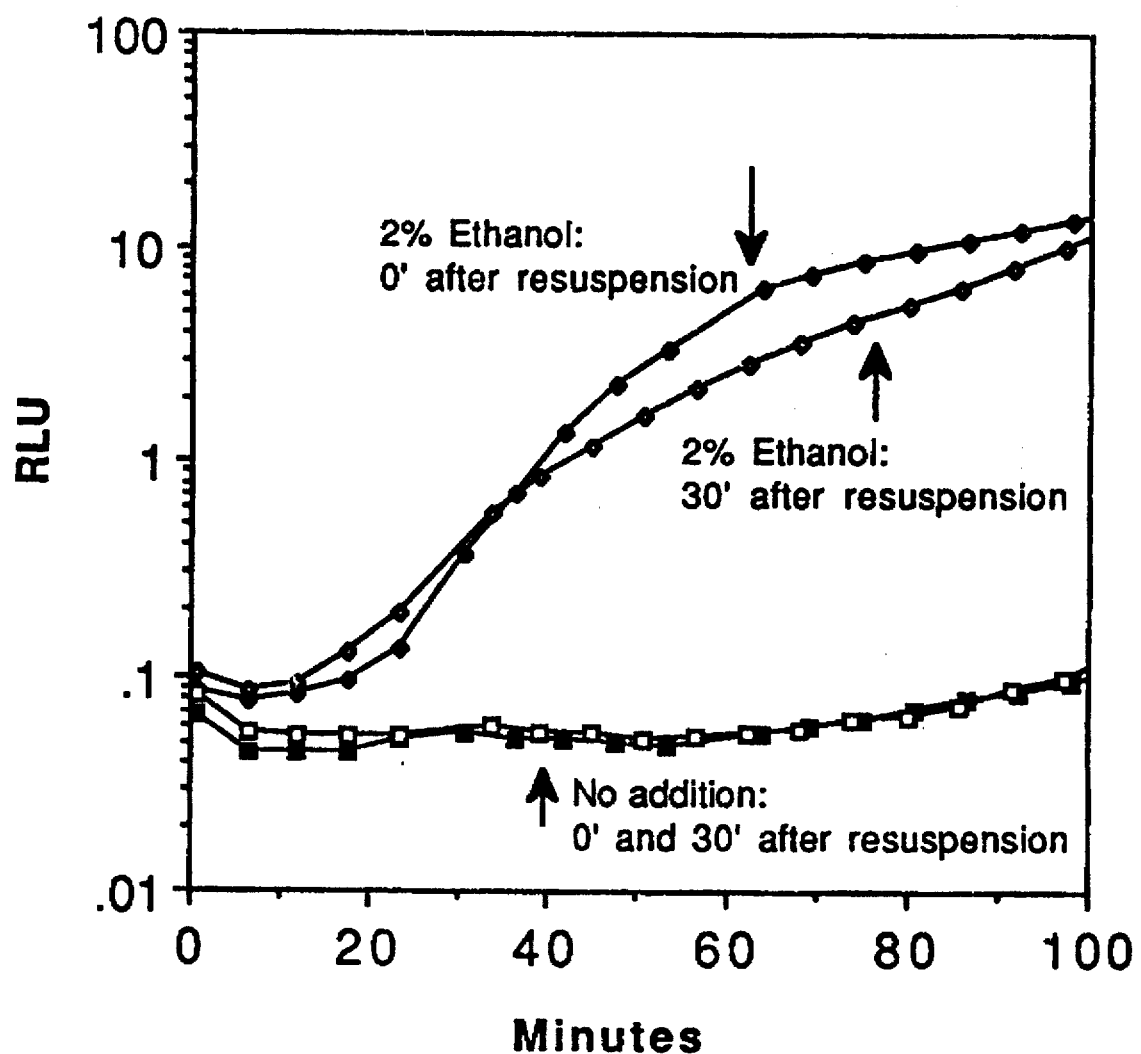

United States Patent [19]
Vandyk et al.

[11] Patent Number: 5,731,163
[45] Date of Patent: Mar. 24, 1998

[54] LYOPHILIZED BIOLUMINESCENT BACTERIAL REAGENT FOR THE DETECTION OF TOXICANTS

[75] Inventors: Tina Kangas Vandyk, Wilmington; Lorraine Winona Wagner, Newark, both of Del.

[73] Assignee: E. I. du Pont de Nemours and Company, Wilmington, Del.

[21] Appl. No.: 755,776

[22] Filed: Nov. 22, 1996

Related U.S. Application Data

[63] Continuation of Ser. No. 344,428, Nov. 23, 1994, abandoned.

[51] Int. Cl.$^6$ ............................ C12N 1/21; C12N 15/00; C12Q 1/66; C12Q 1/68
[52] U.S. Cl. ........................... 435/7.32; 435/6; 435/8; 435/252.3; 935/72; 935/73
[58] Field of Search ...................... 435/6, 7-32, 8, 435/252.3; 935/72, 73

[56] References Cited

U.S. PATENT DOCUMENTS 3,843,517   10/1974   McKinney et al. ............ 210/611

FOREIGN PATENT DOCUMENTS

| | | |
|---|---|---|
| WO 94/01584 | 1/1984 | WIPO. |
| WO 90/08836 | 8/1990 | WIPO. |
| WO 92/18642 | 10/1992 | WIPO. |
| WO 94/13831 | 6/1994 | WIPO. |

OTHER PUBLICATIONS

Fernandez–Pinas et al. Expression of luxCD–E in Anabaena sp. can replace the use of exogenous aldehyde for in vivo localization of transcripton by luxAB. Gene. 150:169–174, 1994.

Marincs et al. Immobilization of *Escherichia coli* expressing the *lux* genes of *Xenorhabdus luminescens*. Applied and Environmental Microbiology. 60(10):3862–3863. 1994.

Selifonova et al. Bioluminescent sensors for detection of bioavailable Hg(II) in the environment. Applied and Environmental Microbiology. 59(9):3083–3090. 1993.

Corbisier, P. et al, "Construction and Development of Metal Ion Biosensors", *J. of Bioluminescence and Chemiluminescence*, 9(5), 313 (Abstract, 8th Int'l Symp. on Bioluminescene and Chemiluminescence, Poster 03, Sep./Oct. 1994.

Yates, I.E. et al, "Bacterial Bioluminscence as a Bioassay for Mycotoxins", *Applied & Environmental Microbiology*, 44(5), 1072–1075 (1982).

Sherr, B. et al., "Use of Monodispersed Fluorescently Labeled Bacteria to Estimate In–Situ Protozoan Bacterivory", *Applied Environmental Microbiology*, 53 (5) (1987) pp. 958–965.

Rosson, R. A., Biluminescence for Detection of Trace Coompounds. Govt. Reports announncements & Index, Issue 09, (1990) pp. 1–7.

Park, S–F., Stewart, G.S.A.B., and Kroll, R–G, 1992. The use of Bacterial Luciferase for Monitoring the Environment Regulation of Expression of Genes Encoding Virulence Factors, in *Listeria Monocytogenes* J. Gen. Microbiol. 138:2619–2627.

Janda, I, and Opekarova, M. 1989, Long–term Preservation of Active Lumunous Bacteria by Lyophilization, Journal of Bioluminescence and Chemiluminescence, vol. 3:27–29.

*Primary Examiner*—Douglas W. Robinson
*Assistant Examiner*—Thanda Wai

[57] ABSTRACT

A reagent, useful in the detection of environmental insults comprising bacterial cells containing a stress promoter operably linked to a lux gene complex has been prepared by lyophilizing the cells in a specified medium. The reagent may be used immediately upon rehydration where a positive test for the presence of an environmental insult is given by an increase in light production from the cells.

8 Claims, 1 Drawing Sheet

5,731,163

LYOPHILIZED BIOLUMINESCENT BACTERIAL REAGENT FOR THE DETECTION OF TOXICANTS

This is a continuation of application Ser. No. 08/344,428 filed 23 Nov. 1994, now abandoned.

FIELD OF INVENTION

The present invention relates to a method for the detection of sublethal levels of environmental insults using a lyophilized bioluminescent bacteria as a test reagent.

TECHNICAL BACKGROUND

Increasing public concern and mounting government regulations have provided impetus for the development of environmental sensing systems capable of detecting contaminants in soil and ground water. Highly sensitive and specific detection systems incorporating analytical tools such as Gas Chromatography and Mass spectro-photometry have been known for several years; however, these systems require expensive equipment and skilled operators. Moreover, sample preparation and data analysis is often cumbersome and time consuming.

Toxicity assays involving living organisms such as Daphnia, used in the standard U.S. water toxicity test, are simpler; however, these tests are non-specific and not particularly rapid. Somewhat more rapid are cell based toxicity assays that incorporate a bacterial cell as the sensitive element. These systems use bacterial cells as a reagent in a conventional automated analytical system. For example the RODTOX system (Central Kagaku., Tokyo, Japan) is a batch assay that measures bacterial oxygen consumption and was designed for use in sewage plants. Other bacteria based systems such as the GBI TOXALARM system (Genossenschaft Berliner Ingenieuirkollective, Berlin, Germany) can measure the presence of specific chemicals. The GBI TOXALARM is known to be able to detect the presence of as little as 0.1 ppm potassium cyanide in a sample. These detection systems are useful, but are hampered by cumbersome and complex detection systems. Recently, the phenomenon of bacterial bioluminescence has been regarded as providing a simpler and more sensitive mode of detection in environmental sensing systems.

Bacterial bioluminescence is phenomenon in which the products of 5 structural genes (luxA, luxB, luxC, luxD and luxE) work in concert to produce light. Naturally bioluminescent organisms have been used as the sensitive element in toxicity tests. The MICROTOX system, (Microbics Corp., Carlsbad, Calif.) is an example. The MICROTOX system measures the natural baseline luminescence of Photobacterium phosporeum and relates this to the hostility of the environment around the organism. Since the three couples, ATP level, NADPH level and $FMNH_2$ level, between light production and the central metabolic events of energy generation are necessary for light production in *Photobacterium phosporeum*, any insult that interferes with the availability or interaction of these metabolites will cause a decrease in the activity of the bioluminescence(lux) system and therefore a related decrease in light production by the organism.

A main attribute of bioluminescent systems is that the decrease in light production is rapid, occurring within minutes of exposure to an insult. Another key advantage of these systems is that light detection can be exquisitely sensitive (down to the level of single photons), and is readily adaptable to portable field units. Furthermore, the logistics of light detection precludes the necessity of having the detector contact a wet, biological sample, which is a key weakness in competing technologies (such as ion-selective electrodes), where detector fouling and corrosion are responsible for significant down time.

Although the MICROTOX and similar systems are useful, their sensitivity is limited to detecting levels of insults that kill or cripple the cell metabolically. To be detected by these systems, the insult must have reached a level high enough to either interfere with the central metabolism of the cell or to inactivate the Lux proteins.

Frequently it is necessary to be able to detect levels of insults at levels below those needed to affect cell metabolism. Such is the case in waste treatment facilities where lethal concentrations of pollutants can eradicate the useful microbial population, incurring significant cost and plant down time. A preferred sensing system would be one that would be able to detect the presence of insults at sublethal levels, before a useful microbial population could be harmed. Such an early warning could be used to trigger prompt remedial action to save the indigenous microbial population.

Recently recombinant bacteria have been developed by fusing the lux structural genes to chemically responsive bacterial promoters and then placing such chimeras in appropriate hosts. These recombinant bacteria are sensor organisms that glow in response to specific stimuli. An example of this type of gene fusion is described by H. Molders (EP 456667). Here, indicator bacterial strains are provided (by vector mediated gene transfer) containing a met promoter, specifically inducible by Hg ions, fused to a bacterial luciferase (lux AB) gene complex which is responsible for bioluminescence. The test system of Molders relies on the induction of the mer promoter by the presence of mercury and the subsequent increase in light emission from the recombinant bacteria for the test results.

Recently Applicants have disclosed a method for the detection of environmental insults involving a bacterial detector organism comprising a stress inducible promoter operabaly linked to a lux gene complex (WO 96/16187). A variety of stress promoters were enabled including groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA, micF, and fabA. Each of the stress promoters are sensitive to different classes of environmental stresses, thus permitting a wide array of detection.

One of the principle utilities of such detector organisms is in the monitoring of waste water treatment facilities as well as the testing of environmental samples at remote of isolated sites. For the purposes of field testing it is inconvenient to transport detector organisms to a site for testing all the while maintaining the cells in the appropriate growth condition to allow for maximum sensitivity in detection. A reagent, that could be handled with less stringency would be much more adaptable for remote field use. To that end a number of detection systems that require living cells have attempted to use lyophilized or freeze dried cells as reagents.

Freeze dried or lyophilized cells have been used as reagents in a number of field applications and detection kits. For example McKinney et al., (DE 2100476) demonstrate that freeze-dried microorganism compositions are useful as reagents for the remediation of oil. Cultures of *Candida lipolytica* are freeze-dried and mixed with vermiculite and exposed to an oil layer where the yeast grows rapidly. McKinney demonstrates that cells may be freeze dried and reconstituted and still retain enough viability to function biochemically after a sufficient period of time for acclimation and growth. However, McKinney does not address whether the cells are capable of all normal metabolic functions immediately after reconstitution, and does not teach that mechanisms governing transcription and translation are operational until after a period of acclimation and cell growth.

Yates (*Appl. Environ. Microbiol.*, 44, 1072, (1982) disclose a method for the detection of mycotoxins involving the use of the naturally bioluminescent Photobacterium phosphoreum. The concentrations of mycotoxins causing 50% light reduction (EC50) in *Photobacterium phosphoreum* were determined immediately and at 5 h after reconstitution of the bacteria from a dried state. Yates determines the presence of mycotoxins on the basis of a reduction in light from the photobacterium, and notes that higher concentrations are needed to produce a 50% reduction in light at 0 hr. post rehydration.

Yates shows that a reduction in light production is possible from Photobacterium in response to the presence of mycotoxin immediately after freeze dried are reconstituted. However, since the metabolic requirements for light production in Photobacterium do not require synthesis of new proteins, Yates does not address whether translational and transcriptional elements are functional in cells 0 hr. post rehydration.

Recently Corbisier et al., (*J. Biolumin. Chemilumin.*, 9, 289, (1994)) have disclosed a genetically engineered Alcaligenes bacteria comprising several metal sensitive promoters fused with a lux gene complex from either *V. fischeri* or *V. harveyi*, useful as microbial bioluminescent sensors for the detection of metals. Corbisier has demonstrated that these cells may be lyophilized and reconstituted without adversely affecting the cellular bioluminescent apparatus. However, the method of Corbisier still allows for a significant period of time for cell acclimation before the cell sensor is used.

The above methods demonstrating the use of freeze dried cells as biological reagents have shown that freeze dried cells may retain their metabolic activity after rehydration, however, appear to require a period of time of acclimation and growth for full metabolic abilities to return. Applicants have previously shown that bacterial cells transformed with plasmid containing a stress promoter operably linked to a lux gene complex were useful as detector organisms in a method for the detection of environmental stresses and toxicants. The mechanism postulated is that the presence of an environmental toxicant activates the stress promoter which in turn drives the lux gene complex to synthesize new proteins responsible for light production by the cell. The presence of the insult or toxicant is determined on the basis of an increase in light production (in contrast to the decrease seen in Yates supra) and requires new protein synthesis.

Applicants have now made the surprising discovery that these stress detector cells may be freeze dried and upon rehydration are immediately useful in a method for the detection of environmental insults. The ability of these cells to be used immediately, after rehydration is surprising since, to date, no freeze dried cell has been taught that demonstrates the level of metabolic activity needed to synthesize new proteins so soon after rehydration. In all other instances cells must be subject to a period of acclimation, or initial growth before new protein synthesis is seen. For example, in the method of Yates supra, light production is seen to decrease in response to the presence of a mycotoxin, immediately after rehydration. However, the metabolic requirements needed for a test using a naturally bioluminescent cell (Photobacterium) which relies on a decrease of light production, is only for the presence of active Lux proteins, reducing potential (NADH) and ATP. In contrast, the requirements for a test using a detector cell that relies on genetic regulation for light production include the presence of active Lux proteins, ATP,CTP, TTP and GTP, RNA polymerase and all requirements for translation and transcription. Hence the requirements of the cells within Applicants' invention are far more stringent that of those taught in the art.

SUMMARY OF THE INVENTION

Disclosed is a method for detecting the presence of an environmental insult with a lyophilized biological reagent said reagent comprising a detector organism containing an expressible lux gene complex under the control of a stress inducible promoter sequence, the method comprising the steps of:

(i) rehydrating the lyophilized biological reagent in a suitable amount of water wherein a baseline bioluminescence is produced;

(ii) immediately contacting the rehydrated reagent with a sample suspected of containing an environmental insult to form a reagent mixture;

(iii) incubating the mixture for at least 20 minutes and at a temperature of up to 30° C. and;

(iv) detecting a change in bioluminescence from the mixture.

The method can be used with a sample containing a diverse microbial population and includes embodiments wherein the change in bioluminescence of step (iv) are increases or decreases in bioluminescence. A stress inducible promoter may be selected from the group consisting of groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA, micF, and fabA.

Also disclosed is a lyophilized biological reagent comprising a transformed bacteria containing an expressible lux gene complex under the control of a stress inducible promoter sequence.

The invention also concerns a kit containing the lyophilized biological reagents disclosed herein along with suitable solvents and/or buffers. A preferred embodiment for detecting the presence of an environmental insult comprises the following in packaged combination:

(i) an aliquoted lyophilized biological reagent comprising:
   (a) a detector cell containing a DNA fragment comprising a stress promoter gene operably linked to the lux gene complex;
   (b) a suitable buffer; and
   (c) a cryoprotective reagent;

(ii) a rehydrating reagent; and (iii) a suitable growth media.

The kit can further include a means for measuring light output from the biological reagent.

BRIEF DESCRIPTION OF THE FIGURES

FIG. 1 is a plot of Relative Light Units over time showing the induction of the stress response from reconstituted lyophilized cells.

DETAILED DESCRIPTION OF THE INVENTION

As used herein the following terms may be used for interpretation of the claims and specification.

The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

A "fragment" constitutes a fraction of the DNA sequence of the particular region.

"Nucleic acid" refers to a molecule which can be single stranded or double stranded, composed of monomers (nucleotides) containing a sugar, phosphate and either a purine or pyrimidine. In bacteria and in higher plants, "deoxyribonucleic acid" (DNA) refers to the genetic material while "ribonucleic acid" (RNA) is involved in the translation of the information from DNA into proteins.

The term "transformation" refers to the acquisition of new genes in a cell after the incorporation of nucleic acid.

The term, "operably linked" refers to the fusion of two fragments of DNA in a proper orientation and reading frame to be transcribed into functional RNA.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the above-mentioned gene product if the gene product is a protein.

The term "bioluminescence" refers to the phenomenon of light emission from any living organism.

The term "lux" refers to the lux complex of structural genes which include luxA, luxB, luxC, luxD and luxE and which are responsible for the phenomenon of bacterial bioluminescence. A lux gene complex might include all of the independent lux genes, acting in concert, or any subset of the lux complex.

The term "stress" or "environmental stress" refers to the condition produced in a cell as the result of exposure to an environmental insult.

The term "insult" or "environmental insult" refers to any substance or environmental change that results in an alteration of normal cellular metabolism in a bacterial cell or population of cells. Environmental insults may include, but are not limited to, chemicals, environmental pollutants, heavy metals, changes in temperature, changes in pH as well as agents producing oxidative damage, DNA damage, anaerobiosis, changes in nitrate availability or pathogenesis.

The term "stress response" refers to the cellular response resulting in the induction of detectable levels of stress proteins.

The term "stress protein" refers to any protein induced as a result of environmental stress or by the presence of an environmental insult. Typical stress proteins include, but are not limited to those encoded by the genes groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA, micF, and fabA.

The term "stress gene" refers to any gene whose transcription is induced as a result of environmental stress or by the presence of an environmental insult. Typical E. coli stress genes include, but are not limited to groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA, micF, and fabA.

The term "heat shock gene" refers to any gene for which its synthesis is positively controlled by the structural gene encoding the sigma-32 protein (rpoH).

The term "stress inducible promoter" refers to any promoter capable of activating a stress gene and causing the expression of the stress gene product.

The term "detector organism" refers to an organism which contains a gene fusion consisting of a stress inducible promoter fused to the lux gene complex and which is capable of expressing the lux gene products in response to an environmental insult. Typical detector organisms include but are not limited to bacteria.

The term "lyophilized biological reagent" refers to a detector organism which contains a gene fusion consisting of a stress inducible promoter fused to the lux gene complex and which is freeze-dried in a specific medium and is capable of expressing the lux gene products in response to an environmental insult, immediately upon rehydration.

The term "lyophilize" or "lyophilization" or "freeze-dry" will refer to a process for the removal of water from frozen bacterial cultures by sublimation under reduced pressure.

The term "rehydration" or "reconstitution" will refer to the process whereby a specified amount of liquid, usually sterile water or growth media is added to a sample of lyophilized biological reagent resulting in the rejuvenation of detector organisms to a point where metabolic activity may be detected.

The term "Relative Light Unit" is abbreviated "RLU" and refers to a measure of light emission as measured by a luminometer, calibrated against an internal standard unique to the luminometer being used.

The present invention provides a method for the detection of environmental insults, such as chemical toxicants, at levels that are sublethal to the detector organism. The method incorporates a lyophilized biological reagent, the active part of which is the detector organism. The detector organism comprises a stress promoter operably linked to a lux gene complex so that when the detector organism comes in contact with the environmental insult the stress promoter is activated resulting in the production of the Lux proteins and the production of light from the organism. Unique to the present method is the fact that the lyophilized reagent containing the detector organism may be used immediately after reconstitution for detection without any acclimation or growth stabilization.

This invention is anticipated to have broad applicability. Potential uses include monitoring of air and water quality, agrochemical and pharmaceutical design, manufacturing and fermentation process control, process monitoring and toxicity screening. These applications may benefit many enterprises including the chemical, beverage, food and flavor, cosmetics, agricultural, environmental, regulatory and health care industries. The method and reagent of the present invention is particularly useful in the monitoring of any area or media for the presence of sublethal levels of environmental toxicants. For example it is contemplated that the present invention will be particularly useful in the monitoring of the influx at waste water treatment facilities which is key to preventing contaminants from destroying the active microbial population in such facilities. Further, the lyophilized biological reagent is particularly adaptable for field testing of soil and ground water in and around both commercial and domestic sites where pollutants may pose a hazard.

Environmental insults capable of being detected by the detector organism of the present invention include a variety of organic and inorganic pollutants commonly found in industrial sites, waste streams and agricultural run-off. Such compounds include but are not limited to the polyaromatic hydrocarbons (PAH), the halogenated aromatics as well as a variety of heavy metals such as lead, cadmium, copper, zinc, and cobalt. Compounds demonstrated to be detected by the method of the present invention include atrazine, benzene, copper sulfate, 2,4-dichlorophenoxyacetic acid, ethanol, methanol, 2-nitrophenol, 4-nitrophenol, pentachloro-phenol, phenol, toluene, dimethylsulfoxide, lead nitrate, cadmium chloride, sodium chloride, acetate, propionate, hydrogen peroxide, puromycin, mercury chloride, 2,4-dichloroanaline, propanol, butanol, isopropanol, methylene chloride, Triton X100, acrylamide, methyl viologen, mitomycin C, menadione, ethidium bromide, serine hydroxamate and xylene. Other environmental stresses detected included low phosphate levels, poor nitrogen source, poor carbon source and irradiation with ultraviolet light.

Reporter genes:

The preferred reporter gene for the present invention is the lux gene complex, responsible for bacterial bioluminescence and isolated from the bacteria *Vibrio fischeri*. Bacterial bioluminescence is phenomenon in which the products of 5 structural genes (luxA, luxB, luxC, luxD and luxE) work in concert to produce light. The luxD product generates a $C^{14}$ fatty acid from a precursor. The $C^{14}$ fatty acid is activated in an ATP dependent reaction to an acyl-enzyme conjugate through the action of the luxE product which couples bacterial bioluminescence to the cellular energetic state. The acyl-enzyme (luxE product) serves as a transfer agent, donating the acyl group to the luxC product. The acyl-LuxC binary complex is then reduced in a reaction in which NADPH serves as an electron pair and proton donor reducing the acyl conjugate to the $C^{14}$ aldehyde. This reaction couples the reducing power of the cell to bacterial light emission. The light production reaction, catalyzed by luciferase (the product of luxA and luxB), generates light. The energy for light emission is provided by the aldehyde to fatty acid conversion and $FMNH_2$ oxidation, providing another couple between light production and the cellular energy state.

The source of the bacterial lux complex was the pUCD615 plasmid containing the lux gene complex, fully described by Rogowsky et al. (*J. Bacteriol.* 169 (11) pp 5101–512, (1987)).

Stress Promoters: The present invention provides a stress inducible promoter sensitive to the presence of an environmental insult. Stress inducible promoters from both prokaryotic and eukaryotic cells may be used however promoters from bacteria are preferred and promoters from *E. coli* are most preferred. Suitable stress inducible promoters may be selected from, but are not limited to the list of genes under the heading "responding genes" given in Table I, below:

TABLE I

| STIMULUS | REGULATORY GENE(S) | REGULATORY CIRCUIT | RESPONDING GENES* |
|---|---|---|---|
| Protein Damage[a] | rpoH | Heat Shock | grpE, dnaK, lon, rpoD, groESL, lysU, htpE, htpG, htpI, htpK, clpP, clpB, htpN, htpO, htpX, etc. |
| DNA Damage[b] | lexA, recA | SOS | recA, uvrA, lexA, umuDC, uvrA, uvrB, uvrC, sulA, recN, uvrD, ruv, dinA, dinB, dinD, dinF, etc. |

TABLE I-continued

| | | | |
|---|---|---|---|
| Oxidative Damage[c] | oxyR | Hydrogen Peroxide | katG, ahp, etc. |
| Oxidative Damage[d] | soxRS | Superoxide | micF, sodA, nfo, zwf, soi, etc. |
| Membrane Damage[e] | fadR | Fatty Acid Starvation | fabA |
| Any[f] | ? | Universal Stress | uspA |
| Stationary Phase[g] | rpoS | Resting State | xthA, katE, appA, mcc, bolA, osmB, treA, otsAB, cyxAB, glgS, dps, csg, etc. |
| Amino Acid Starvation[h] | relA, spoT | Stringent | his, ilvBN, ilvGMED, thrABC, etc. |
| Carbon Starvation[i] | cya, crp | Catabolite Activation | lac, mal, gal, ara, tna, dsd, hut, etc. |
| Phosphate Starvation[j] | phoB, phoM, phoR, phoU | P Utilization | phoA, phoBR, phoE, phoS, aphA, himA, pepN, ugpAB, psiD, psiE, psiF, psiK, psiG, psiL, psiJ, psiN, psiR, psiH, phiL, phiO, etc. |
| Nitrogen Starvation[k] | glnB, glnD, glnG, glnL | N Utilization | glnA, hut, etc. |

*Genes whose expression is increased by the corresponding stimulus and whose expression is controlled by the corresponding regulatory gene(s).
[a]Neidhardt and van Bogelen in *E. coli* and *Salmonella typhimurium*; Cellular and Molecular Biology (Neidhardt, F. C., et al. Eds., pp. 1334–1345, American Society of Microbiology, Washington, DC (1987))
[b]Walker in *E. coli* and *Salmonella typhimurium*; Cellular and Molecular Biology (Neidhardt, F. C., et al. Eds., pp. 1346–1357, American Society of Microbiology, Washington, DC (1987))
[c]Christman et al. Cell 41: 753–762 (1985); Storz et al. Science 248: 189–194 (1990); Demple, Ann. Rev. Genet. 25: 315–337 (1991)
[d]Demple, Ann. Rev. Genet. 25: 31 337 (1991)
[e]Magnuson et al. Microbiol. Rev 57: 522–542 (1993)
[f]Nystrom and Neidhardt, J. Bacteriol, 175: 2949–2956 (1993); Nystrom and Neidhardt (Mol. Microbiol. 6: 3187–3198 (1992)
[g]Kolter et al. Ann. Rev. Microbiol. 47: 855–874 (1993)
[h]Cashel and Rudd in *E. coli* and *Salmonella typhimurium*; Cellular and Molecular Biology (Neidhardt, F. C., et al. Eds., pp. 1410–1438, American Society of Microbiology, Washington, DC (1987)); Winkler in *E. coli* and *Salmonella typhimurium*; Cellular and Molecular Biology (Neidhardt, F. C., et al. Eds., pp. 395–411, American Society of Microbiology, Washington, DC (1987))
[i]Neidhardt, Ingraham and Schaecter. Physiology of the Bacterial Cell: A Molecular Approach, Sinauer Associates, Sunderland, MA (1990), pp 351–388; Magasanik and Neidhardt in *E. coli* and *Salmonella typhimurium*; Cellular and Molecular Biology (Neidhardt, F. C., et al. Eds., pp. 1318–1325, American Society of Microbiology, Washington, DC (1987))
[j]Wanner in *E. coli and Salmonella typhimurium*; Cellular and Molecular Biology (Neidhardt, F. C., et al. Eds., *E. coli* and *Salmonella typhimurium*; Cellular and Molecular Biology (Neidhardt, F. C., et al. Eds., pp. 1326–1333, American Society of Microbiology, Washington, DC (1987))
[k]Rietzer and Magasanik in *E. coli* and *Salmonella typhimurium*; Cellular and Molecular Biology (Neidhardt, F. C., et al. Eds., pp. 1302–1320, American Society of Microbiology, Washington, DC (1987)); Neidhardt, Ingraham and Schaecter. Physiology of the Bacterial Cell: A Molecular Approach, Sinauer Associates, Sunderland, MA (1990), pp 351–388

Table I indicates the relationship of responding gene(s) with a particular regulatory gene(s) and a regulatory circuit and the associated cellular stress response triggered by a particular stimulus.

Vectors

The invention also provides a transformation vector containing a stress inducible promoter-lux gene fusion, capable of transforming a bacterial host cell for the expression of the Lux proteins. A variety of transformation vectors may be used, however, those capable of transforming E. coli are preferred. pGrpELux.3, and pGrpELux.5 are two specific examples of suitable transformation vectors whose construction is given in detail in the following text. These vectors represent only a sample of the total number of vectors created for the purpose of introducing stress promoter-lux reporter fusions into host cells. However, it will be readily apparent to one of skill in the art of molecular biology that the methods and materials used in their construction are representative of all other suitable vectors.

pGrpELux.3 and pGrpELux.5 are vectors containing the grpE promoter. pGrpELux.3 and pGrpELux.5 were created by the method of direct cloning. Transformation vectors such as these are common and construction of a suitable vector may be accomplished by means well known in the art. The preferred source of the lux genes is a pre-existing plasmid, containing a promoterless lux gene complex. Similarly, preferred sources of the stress inducible promoter DNA for the construction of the transformation vector are either also a pre-existing plasmid, where the stress inducible promoter DNA is flanked by convenient restriction sites, suitable for isolation by restriction enzyme digestion, or the product of a PCR reaction.

The pGrpELux.3 and pGrpELux.5, vectors are constructed from the E. coli stress gene grpE, and the lux gene complex. pGrpE4 is an E. coli vector derived from pUC18 (Pharmacia, Cat. No. 27-4949-01). pGrpE4 contains the grpE gene, including its promoter, bounded at the 5' end by an EcoRI site and at the 3' end by a BbuI site. Additionally, the grpE promoter is bounded at the 3' end by a PvuII site and an HaeIII site just downstream of the EcoRI site (FIG. 2). Digestion with EcoRI and BbuI restriction enzymes yields a 1.1 kb fragment which corresponds to the grpE gene. Further digestion with PvuII produces two fragments, one of which contains the grpE promoter. The 3' PvuII site on the grpE promoter fragment is converted to an EcoRI site via ligation to phosphorylated EcoRI linkers. Further digestion by HaeIII yields a grpE promoter fragment conveniently bounded by a 5' HaeIII site and a 3' PvuII site (FIG. 2).

The pUCD615 plasmid containing the lux gene complex is fully described by Rogowsky et al. (J. Bacteriol, 169 (11) pp 5101–512, (1987)). Plasmid pUCD615 is a 17.6 kb plasmid which contains the genes for kanamycin and ampicillin resistance and contains the promoterless lux gene operon (FIG. 2). pUCD615 is first digested with restriction enzymes EcoRI and SmaI, opening the plasmid, followed by ligation with the DNA fragments from the HaeIII digestion of pgrpE IV.

Typically, the products of the ligation reactions are screened by first transforming a suitable host and screening for bioluminescence. A variety of hosts may be used where hosts having high transformation frequencies are preferred. XL1Blue (Stratagene, LaJolla, Calif.) and DH5-α (GIBCO-BRL, Gaithersburg, Md.) are two such hosts. Preferred methods of bioluminescence screening involve exposing gridded cultures of transformants to a suitable X-ray film, followed by visual analysis of the developed films for evidence of exposure. Reisolation of the plasmid from the transformed host and restriction digests followed by gel electrophoresis is used to confirm the existence of the correct plasmid. The plasmids pGrpELux.3 and pGrpELux.5, isolated from two different transformed colonies, are indistinguishable on the basis of restriction enzyme analysis. Under some experimental conditions cells transformed with pGrpELux.5 exhibited higher baseline bioluminescence than those transformed with pGrpELux.3 and hence pGrpELux.5 is preferred for the detection of many environmental insults.

Transformed Hosts—Detector Organisms:

The present invention further provides a transformed host cell capable of increased luminescence in the presence of an environmental insult. Many suitable hosts are available where E. coli is preferred and the E. coli strain RFM443 is most preferred. RFM443 is derived from W3102 which is fully described by B. Bachmann, in E. coli and Salmonella typhimurium; Cellular and Molecular Biology (Niedhardt et al. Eds., pp 1190–1220, American Society of Microbiology, Washington, D.C. (1987)). Transformation of RFM443 by pGrpELux.3 gives the new strain TV1060 which has been deposited with the ATCC under the terms of the Budapest Treaty. Transformation of RFM443 by pGrpELux.5 gives the new strain TV1061. The baseline of bioluminescence from strain TV1061 is greater than that from strain TV1060. E. coli TV1060 has been assigned ATCC No. 69142, and TV1061 has been assigned ATCC No. 69315.

It is well known that hydrophobic compounds are effectively excluded by the cell envelope from entry into gram negative bacteria, such as E. coli. Recently several E. coli strains containing a mutation for tolerance to colicins (tolC-) have been found to have the unexpected additional property of increased permeability of host cell envelopes to various organic molecules. (Schnaitman et. al. J. Bacteriol., 172 (9), pp 5511–5513, (1990)). Optionally, it is within the scope of the present invention to provide a transformed bacterial host containing the tolC- mutation as a suitable detector organism.

Reagent Preparation—Cell lyophilization:

Methods of preserving cells are varied and well known in the art (Maintenance of Microorganisms Kirsop, B. E., and Snell J. J. S., Eds. (1984), Academic Press, New York). The method chosen will depend on such factors as cell viability, genetic mutations, frequency of culture use and others. For cultures whose primary utility is use in field tests an kits, drying, freeze drying (lyophilization) or freezing are the most suitable. Although it is contemplated that any of these methods are compatible with the present invention the method most preferred is lyophilization. Lyophilization of cultures is a process that involves the removal of water from frozen cultures by sublimation under reduced pressure.

When freeze drying living organisms several elements must be taken into account to allow for both the maximum viability and maximum storage time for the cells. At the time of harvesting cultures should be healthy and actively growing in either the logarithmic or early stationary phase and at a density of about $10^8$/ml. A basic requirement in the medium for the preservation of the cells is a cryoprotective agent. A variety of cryoprotective reagents are known including skim milk, sucrose, dextran, horse serum, and inositol. For the purpose of the present invention sucrose is preferred at a concentration of about 12%.

The choice of media and cryoprotective agents is an empirical process and a choice is made on the basis of highest cell viability and storage parameters. In the present application four different combinations of media and cryoprotective reagents were analyzed for their effect on cell viability, onset of induction of bioluminescence, and stability of baseline luminescence. The four lyophilization media are listed below:

A. LB media with glucose (1%)

B. Minimal Media with casamino acids (2%) and glucose (1%)

C. Minimal Media with casamino acids (2%), glucose (1%), and sucrose (12%)

D. Minimal media with casamino acids (2%), glucose (1%), and skim milk (12%).

Of the above media it was found that lyophilization media (C) gave the best cell viability in combination with rapid onset of bioluminescent inducibility and stability of baseline luminescence.

In the present method cells were grown to about an absorbance of 2 at O.D. 600 (Log-phase growth) in LBG broth containing kanamycin and portions of the culture were subcultured into lypohilization media (D) above and grown until again reaching log phase densities. At this point cells were harvested by centrifugation, resuspended in lyophilzation media and frozen at -70° C. in a lyophilization vial. Vials were placed on the lyophilizer and lyophilized for at least 3 hours at ≤20 millitorrs and -100° C. Vials were sealed and stored at refrigerated or freezer temperatures until rehydrated.

In order to rehydrate the lyophilized cells for use in the test method, lyophilized reagent was resuspended in a volume of sterile water equal to the volume of the samples prior to lyophilization. Cells were then immediately exposed to a sample suspected of containing an environmental insult and monitored for change in bioluminescence. Bioluminescence is measure on a luminometer of a type similar to that made by Dynatech Laboratories Inc. (Chantilly, Va.)

The following examples are meant to illustrate the invention but should not be construed as limiting it in any way. From the above discussion and these Examples, one skilled in the art can ascertain the essential characteristics of this invention, and without departing from the spirit and scope thereof, can make various changes and modifications of the invention to adapt it to various usages and conditions.

EXAMPLES

General Methods

*E. coli* TV1061 contains a plasmid with the *E. coli* grpE heat shock promoter fused to the *Vibrio fischeri* luxCDABE reporter genes and are fully described in the DETAILED DESCRIPTION section, above. Materials and Methods suitable for the maintenance and growth and lyophylization of bacterial clutures may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), pp. 210–213. American Society for Microbiology, Washington, D.C. All reagents and materials used for the growth, maintenance and lyophilization of bacterial cells were obtained from Diffco Laboratories or Sigma Chemical Company unless otherwise specified.

Example 1

Preparation of Lyophilized Biological Reagent

Example 1 describes the preparation of the biological reagent by the process of lyophilization in specially formulated media.

*E. coli* TV1061 cells were grown in LBG broth containing the following components in g/L: tryptone, 10; yeast extract, 5; sodium chloride, 10; glucose, 10 and Kanamycin at a final concentration of 2.5 g/L. Cultures were allowed to grow to mid-log phase at O.D.600 of 2.

This culture was then used to inoculate the production medium consisting of the following ingredients (g/L): ammonium sulfate, 0.3; magnesium sulfate, 0.45; sodium citrate dihydrate 0.047; ferrous sulfate seven hydrate, 0.025; thiamine-HCl 0.06; potassium phosphate dibasic, 1.95; sodium phosphate monobasic, 0.9; biotin 0.005; casamino acids, 20.0; trace element solution, 1 mL stock; uracil 0.1; glucose, 20.o; calcium chloride dihydrate, 0.026.

Trace element solution was composed of the following (g/L): zinc sulfate seven hydrate, 8; copper sulfate five hydrate, 3; manganese sulfate monohydrate, 2.5; boric acid, 0.15; ammonium molybdate four hydrate, 0.1; cobalt chloride six hydrate, 0.06.

Production culture was grown at 26° C., pH 7.0, Dissolved oxygen (DO2) 50%. Dissolved oxygen was controlled by increasing agitation and aeration during growth. (rpm 300–1200; aeration 100–300 L/H). When cultures reached an OD 600 of 1.8 (logarithmic growth), they were harvested by centrifugation (Sorvall Superspeed, 9000 rpm for 20 minutes, 4 C). Medium was decanted and cells were kept on wet ice. Cell pellets were resuspended in half the volume of the starting culture with fresh production medium and an equal half volume of 24% sterile sucrose. Cells were resuspended and dispensed into sterile lyophilization vials. Vials were frozen at -70° C. Cultures were kept frozen until the lyophilization process was complete. Vials were placed on the lyophilizer (FD-14-84, FTS Systems, Stone Ridge, N.Y.) using a manifold system and a presterilized filter(Pall Emflon II 0.2 micron absolute) to prevent contamination of culture and lyophilizer. Vials were lyophilized for at least 3 hours at ≤20 millitorrs and -100° C. Vials were sealed and stored at refrigerated or freezer temperatures until rehydrated.

Example 2

Use of Lyophilization Reagent for the Detection of Environmental Stress

Example 2 demonstrates the use of the lyophilized biological reagent for the detection of environmental stress.

The detector organism, *E. coli* TV1061 containing the *E. coil* grpE heat shock promoter fused to the *Vibrio fischeri* luxCDABE reporter genes is grown, harvested and lyophilized as described in Example 1 to prepare the reagent. The reagent was resuspended in a volume of sterile water equal to the volume of the samples prior to lyophilization. Reconstituted cells were tested for their ability to respond to stress induction at three different times post-rehydration. Cells were either used immediately or were incubated for 30 or 60 minutes prior to use. Viable cells were measured by plating serially diluted rehydrated cells on LB plates. Assessment of the ability of cells to respond to stress was made by measuring the kinetic changes in light output following the addition of 20 μl rehydrated cells to 80 μl LB medium with or without 2.5% (v/v) ethanol (final ethanol concentration was 0% or 2%, respectively). Bioluminescence from these treated cells in white microtiter plates (Microlite™, Dynatech Laboratories Inc.) was quantitated in a Dynatech ML3000 microtiter plate luminometer with temperature controlled at 26° C. The units of measurements are relative light units (RLU).

As can be seen by the data in FIG. 1, cells receiving no ethanol maintained a constant baseline luminescence whereas cells in the presence of 2% ethanol demonstrated a 100 fold increase in light output. It is important to note that the cells used at 0 and 30 minutes post-rehydration exhibited similar light production kinetics demonstrating that no acclimation phase is needed for the instant reagent to be effective in this assay.

Example 3

Determination of Lyophilization Media

Example 3 describes the selection of the most appropriate lyophilization media for the bioluminescent detector cell.

E. coli TV1061 cells were grown in LBG broth and inoculated in the production medium as described in Example 1. After growth and harvesting from the production media, cell pellets were resuspended in half the volume of the starting culture in four different media for lyophilization. A. LB media with glucose (1%) B. Minimal Media with casamino acids (2%) and glucose (1%) C. Minimal Media with casamino acids (2%), glucose (1%), and sucrose (12%) D. Minimal media with casamino acids (2%), glucose (1%), and skim milk (12%).

Cells were lyophilized as described in Example 1 and stored for testing. Upon rehydration cells lyophilized in each medium were analyzed for viability, stability of baseline luminescence during the rehydration process and baseline stability during the induction process.

Cell viability was determined by plating the cells after rehydration and determining the number of viable cells on the basis of colony forming units (CFU).

Stability of baseline bioluminescence during rehydration was determined by continuously monitoring the bioluminescence of rehydrated cells over a 30 minute time period. Stability of baseline luminescence during induction was determined by monitoring the bioluminescence of control cells (not exposed to an environmental insult) throughout the time of the test, which was always 120 minutes.

Lag time was determined by measuring the amount of time from induction to the first increase in light output. Average Lag time for healthy, non-lyophilized cells was 20 min.

The results of the analysis are given in Table I below.

cells. Media (C) gave the surprising result of providing cells capable of immediate high level metabolic activity without requiring the almost obligatory acclimation period.

What is claimed is:

1. A method of detecting the presence of a sublethal environmental insult with a lyophilized biological reagent said reagent comprising a detector prokaryotic microorganism containing an expressible luxCDABE gene complex under the control of a stress inducible promoter sequence, the method comprising the steps of:

(i) rehydrating the lyophilized biological reagent in a suitable amount of water wherein a baseline bioluminescence is produced;

(ii) immediately contacting the rehydrated reagent with a sample suspected of containing an environment insult to form a reagent mixture;

(iii) incubating the mixture for at least 20 minutes and at a temperature of up to 30° C. and;

(iv) detecting an increase in bioluminescence from the mixture.

2. The method of Claim 1 wherein said sample contains a diverse microbial population.

3. A method of Claim 1 wherein said lux gene complex is heterologous to the detector organism.

4. A method of Claim 1 wherein the detector organism is a bacteria.

5. The method of Claim 1 wherein the stress inducible promoter is selected from the group consisting of groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA, micF, and fabA.

6. A lyophilized biological reagent comprising bacteria transformed with an expressible luxCDABE gene complex under the control of a stress inducible promoter sequence.

7. A kit for detecting the presence of a sublethal environmental insult comprising the following in packaged combination:

(i) an aliquoted lyophilized biological reagent comprising;

(a) a detector prokaryotic microorganism cell containing a DNA fragment comprising a stress promoter gene operably linked to a luxCDABE gene complex;

(b) a suitable buffer; and (c) a cryo protective reagent;

TABLE I

| Medium | O.D. 600 | Viable Cells/ml | Initial RLU | Lag | Stable During Rehydration | Stable During Induction |
|---|---|---|---|---|---|---|
| A (LBG) | 1.8 | $2.1 \times 10^7$ | 0.0002 | 90 min | YES | NO |
| B (MMG) | 1.8 | $1.9 \times 10^7$ | 0.0001 | 20 min. | NO | NO |
| C (MMGS) | 1.8 | $1.0 \times 10^9$ | 0.066 | 20 min | YES | YES |
| D (MMGSM) | 1.8 | $7.6 \times 10^7$ | 0.0025 | 20 min | YES | NO |

As can be seen by the information in Table I, the only media that demonstrated good stability of light output during both the rehyrdation phase and the induction phase was medium (C). All instances where the baseline was not stable demonstrated a steady increase in light output, presumably due to the increasing health and metabolic activity of the (ii) a rehydrating reagent; and (iii) a suitable growth media.

8. The kit of Claim 7 further including a means for measuring light output from the biological reagent.

* * * * *